United States Patent [19]

Arcuri

[11] Patent Number: 4,626,552

[45] Date of Patent: Dec. 2, 1986

[54] PROCESS FOR THE START-UP OF A FISCHER-TROPSCH REACTOR

[75] Inventor: Kym B. Arcuri, Baton Rouge, La.

[73] Assignee: Exxon Research and Engineering Company, Florham Park, N.J.

[21] Appl. No.: 816,235

[22] Filed: Jan. 6, 1986

[51] Int. Cl.$^4$ .................................................. C07C 1/04
[52] U.S. Cl. .................................... 518/712; 518/706; 518/728
[58] Field of Search ........................ 518/712, 728, 706

[56] References Cited

U.S. PATENT DOCUMENTS 2,847,438 8/1958 Sumerford et al. ................. 518/712

*Primary Examiner*—Howard T. Mars
*Attorney, Agent, or Firm*—Llewellyn A. Proctor

[57] ABSTRACT

A process for the start-up of a reactor which utilizes a feed comprising hydrogen and carbon monoxide for the synthesis of hydrocarbons. The feed is contacted with a bed of hydrocarbon synthesis catalyst in which perturbations of the temperature profile across the bed can develop, and which, at start-up is particularly acute. In practicing the process the feed is introduced into the reactor at a rate ranging up to about 100 percent of the total flow rate at which the feed is introduced to the reactor at line-out. Hydrogen is introduced into the reactor as a portion of said feed at a molar feed rate generally well below the feed rate in which the hydrogen is employed in the reactor at line-out, the molar ratio of hydrogen:carbon monoxide of the feed generally not exceeding about 90 percent, preferably 75 percent, of the molar ratio of hydrogen:carbon monoxide at line-out. While maintaining the low molar ratio of hydrogen:carbon monoxide in the feed, the pressure and temperature of the reactor is raised to levels of pressure and temperature, respectively, employed at line-out. Thereafter the molar ratio of hydrogen:carbon monoxide is raised until the molar ratio of hydrogen:carbon monoxide is essentially that employed at line-out. The thermal stability of the operation is greatly improved, and by conducting start-up in this manner the conventional time period required for start-up can be drastically reduced, e.g., from an 8 to 18 day start-up period for a small reactor to as little as about 20 hours, or less.

14 Claims, 4 Drawing Figures

PROCESS FOR THE START-UP OF A FISCHER-TROPSCH REACTOR

BACKGROUND OF THE INVENTION

I. Field of the Invention

This invention relates to an improved Fischer-Tropsch process for the production of hydrocarbons, especially $C_{10}^+$ distillate fuels, and other valuable products. In particular, it relates to a process for the start-up of a Fischer-Tropsch reactor.

II. Background

A need exists for the creation, development, and improvement of processes useful for the conversion of synthesis gases to hydrocarbons, especially to high quality transportation fuels. Fischer-Tropsch synthesis, a process useful for the synthesis of hydrocarbons from carbon monoxide and hydrogen is well known in the technical and patent literature. The reaction is carried out catalytically by contact of the hydrogen and carbon monoxide with the catalyst, the reaction being accompanied by a large heat release. When this reaction is carried out in fixed-bed reactors, this high heat of reaction results in an increase in the temperature of the catalyst bed above that of the surrounding ambient. This temperatue rise is related to the amount of the occurring reaction and is the driving force for the transfer of heat from the catalyst bed to the surrounding reactor environment. Excessive temperature rises must be avoided in that they can lead to inferior product distribution, and possible temperature runaway which can damage the catalyst.

The Fischer-Tropsch hydrocarbon synthesis reaction is generally carried out in a fixed bed reactor, synthesis gas being fed via an inlet into direct contact with the catalyst while heat is removed from the catalyst bed via heat exchange between the partitioning wall which contains the catalyst and a heat exchange medium, e.g., water. It is advantageous during normal operation to maintain as high a temperature gradient as possible between the bed of catalyst in contact with the partitioning wall and the heat exchange medium used to remove heat from the partitioning wall because this provides the highest space-time-yield (defined as moles of carbon monoxide consumed/volume catalyst-time) with a minimum of reactor volume. The optimum temperature gradient must be one wherein the catalyst produces a product having the desired spectrum of hydrocarbons, while the catalyst bed remains thermally stable.

The temperature gradient between the catalyst bed and heat exchange medium depends upon the volumetric heat release. The temperature gradient also depends upon the space-time-yield, the size (diameter) of the reactor tube, and the heat transfer properties of the bed. From an economic point of view it is desirable to operate the reactor at the highest possible space-time-yield consistent with producing the desired product slate. Though simply stated, this objective is not so easily met in the start-up of a Fischer-Tropsch reactor. In general, when utilizing a ½ inch ID six foot long reactor, it requires from about 8 to 18 days to bring a Fischer-Tropsch reactor "on-stream," or to the point of "line out," i.e., the end of the start-up period, or point where the reactor begins and continues to produce the desired product slate at something approximating the desired space-time-yield. A larger reactor will require a longer period for start-up. Until the reactor lines out the selectivity and yield of product suffer. The productivity of the reactor is very low. The selectivity is less than optimum and the yield is considerably lower than achieved after line-out of the reactor. On top of this, the start-up period requires careful control with highly skilled operating manpower to avoid far more serious, and possibly catastrophic economic losses due to temperature runaway.

The productivity of any given reactor in conducting a Fischer-Tropsch reaction is limited by the amount of heat than can be put into the catalyst bed, and the amount of heat that can be removed from the bed within a given time period. Any change which results in an increase in the reaction rate, or decrease in the heat removal rate will result in an increase in the catalyst bed temperature. A temperature increase will cause a faster reaction rate, and this in turn will produce more heat and a higher temperature. On top of this, in any given catalyst bed the temperature profile across the bed is never entirely uniform. In any given catalyst bed there is invariably a maximum temperature or hot spot at which the local rate of reaction is the greatest, and in Fischer-Tropsch reactions the hot spot is not necessarily at the interface at which the synthesis gas first contacts the catalyst. The hot spot is the most sensitive portion of the reactor with respect to any perturbation in the process variables or heat removal rates of the system. Should the temperature become too highly excessive methane and carbon dioxide will be produced, and should more heat be produced than can be removed by the heat exchange medium for any sustained period the temperature may increase uncontrollably until all of the feed is consumed to produce principally methane and carbon dioxide, or the catalyst deactivated due to the excessive temperature, or both. The extreme temperature of a runaway can destroy the integrity and usefulness of the catalyst located in a hot spot zone and, albeit eventually this portion of a bed may cool due to catalyst inactivation, the excessive heat may cause temperature runaways in other portions of the bed until the entire catalyst bed is completely deactivated. Temperature runaways can cause metallurgical failure of the reactor vessel due to the high temperature and pressure.

In practice, start-up is the most difficult aspect of the Fischer-Tropsch reactor operation. Catalyst beds can readily heat up in localized areas when feed gas is first introduced. During start-up, transient instabilities exist due to the dynamic temperature profiles within and across the catalyst bed. For a given reactor operating with a stable temperature profile, the maximum space-time-yield is controlled by the temperature, pressure, and gas rate since these factors control the rate of carbon monoxide conversion. Under steady state conditions and constant space-time-yield the conventional wisdom is that the ratio of hydrogen:carbon monoxide in the feed gas will not affect the thermal stability of the reactor. Thus, a stable temperature profile is independent of the hydrogen:carbon monoxide feed ratio. The maximum space-time-yield, or volumetric heat release at which a reactor can operate depends entirely upon the heat removal characteristics of the reactor system.

In the start-up of a reactor, if a localized hot spot generates more heat than can be removed, a temperature runaway can occur. With the ratio of hydrogen:carbon monoxide fixed at the desired line-out value, one might therefore raise either the temperature and/or pressure in any combination to finally achieve the desired space-time-yield. However, in practice, the temperature profiles formed when pressure is increased as the last step are extremely unstable and in most cases will lead to a temperature runaway. Consequently, the accepted procedure is to first increase the pressure up to the value desired for normal operation while keeping the temperature at a low value. This minimizes the chances of a thermal runaway since the space-time-yield is kept very low. Once the operating pressure is obtained, the temperature is slowly increased in order to increase the space-time-yield. The procedure, while workable, requires considerable time to bring even a small reactor on-stream, and the reactor lined out to produce the desired product slate at maximum space-time-yield. During the start-up period the productivity, selectivity, and yield are abominable, and careful control by skilled operators is required to avoid temperature runaway.

OBJECTS

It is, accordingly, a primary objective of the present invention to provide an improved, and more stable process for the start-up of an exothermic hydrocarbon synthesis operation.

A more specific object of the invention is to provide a more stable process for the start-up of a hydrocarbon synthesis reactor which can be more rapidly brought on-stream and operated with greatly lowered risk of temperature runaway than conventional hydrocarbon synthesis operations.

Another, and yet more specific object is to provide a process embodying a start-up technique as characterized which will permit a flexible and more effective response to a developing potential temperature runaway situation for the control thereof.

THE INVENTION

These objects and others are achieved in accordance with the present invention embodying a process for the start-up of a reactor wherein a feed comprising an admixture of hydrogen and carbon monoxide is contacted with a bed of hydrocarbon synthesis catalyst in which perturbations of the temperature profile across the bed can develop, and which, at line-out conditions defined by feed flow rate, pressure, temperature, and the molar ratio of hydrogen:carbon monoxide of the feed is sufficient to synthesize hydrocarbons from the hydrogen and carbon monoxide, which generally comprises the steps of: elevating, while maintaining the molar ratio of hydrogen:carbon monoxide in the feed at a low value, the feed flow rate, pressure, and temperature, preferably in that sequence, to values approximating or substantially equal to the line-out feed flow rate, line-out pressure, and line-out temperature, and then gradually increasing the ratio of hydrogen:carbon monoxide in the feed gas to essentially that employed at line-out. By maintaining a very low molar ratio of hydrogen:carbon monoxide in the feed gas, the feed flow rate, pressure, and temperature can be adjusted upwardly to line-out conditions with much greater reactor stability, and far more rapidly than previously possible. Thereafter, the molar ratio of hydrogen:carbon monoxide can be quite readily elevated to line-out conditions, and the reactor brought on-stream and stabilized with much greater facility than previously. The total time of start-up in such operation is drastically reduced as contrasted with conventional operations. Moreover, the use of the molar ratio of hydrogen:carbon monoxide as the ultimate major control variable, rather than pressure and temperature as traditionally used, permits rapid quenching, and restabilization of the reactor system in the event of destabilization brought about by upsets in reactor conditions.

In a more specific and preferred embodiment, the start-up procedure encompasses the steps of:

(i) introducing the feed into the reactor at a rate ranging between about 30 percent and 100 percent, preferably from about 70 percent to about 100 percent, of the total flow rate at which the feed is introduced to the reactor at line-out, hydrogen being introduced into the reactor as a portion of said feed in molar feed rate ranging from about 15 percent to about 90 percent, preferably from about 50 percent to about 80 percent, of the feed rate of hydrogen employed in the reactor at line-out, the molar ratio of hydrogen:carbon monoxide of the feed not exceeding about 90 percent, preferably 75 percent, of the molar ratio of hydrogen:carbon monoxide at line-out.

(ii) raising the pressure and temperature of the reactor to levels of pressure and temperature, respectively, employed at line-out; and, while maintaining these levels of pressure and temperature, (iii) increasing gradually the molar ratio of hydrogen:carbon monoxide until the molar ratio of hydrogen:carbon monoxide is essentially that employed at line-out.

In accordance with this invention, after the introduction of feed into the reactor at the desired flow rate, the pressure in the reactor is increased up to that employed at line-out (and the temperature of the entering feed is increased up to that employed at line-out, or the temperature and then the pressure, or both temperature and pressure alternately are increased up to the pressure and temperature, respectively, employed at line-out), while the molar ratio of hydrogen:carbon monoxide is initially maintained at a very low level, suitably at a molar ratio of hydrogen:carbon monoxide of about 90 percent, preferably 75 percent, of the molar ratio of hydrogen:-carbon monoxide at line-out. It has been found that pressure and temperature (or temperature and pressure) can be increased fairly rapidly up to the pressure and temperature, respectively, employed at line-out, while reactor stability is maintained provided that the molar ratio of hydrogen:carbon monoxide is held at low level until the elevation to line-out or near line-out of pressure and temperature has been accomplished. The molar ratio of hydrogen:carbon monoxide is thereafter gradually increased until the molar ratio of hydrogen:-carbon monoxide reaches line-out.

The hydrogen-carbon monoxide synthesis reaction is very sensitive to temperature and pressure changes when the molar ratio of hydrogen:carbon monoxide in the feed is high. However, temperature and pressure can be readily controlled by maintaining the molar ratio of hydrogen:carbon monoxide in the feed relatively low. Hence, in the start-up of a reactor, the pressure is increased incrementally, generally at an incremental rate of about 10 psig to about 1000 psig, preferably from about 100 psig to about 300 psig per hour, to line-out pressure while the feed ratio of hydrogen:carbon monoxide is maintained at a low value. Line-out pressure ranges generally from about 80 psig to about 600 psig, preferably from about 140 psig to about 400 psig.

The reaction through even more sensitive to temperature changes than pressure changes can also be readily controlled by maintaining a low molar ratio of hydrogen:carbon monoxide in the feed. Hence, in initiating start-up of the reactor the temperature is increased gradually or incrementally, while maintaining a low molar ratio of hydrogen:carbon monoxide in the feed, generally at a rate of about 1 to about 100 Fahrenheit degrees, preferably at a rate of about 10 to about 50 Fahrenheit degrees, per hour, up to or very near the temperature employed at line-out. Line-out temperature ranges generally from about 320° F. to about 560° F., preferably from about 350° F. to about 500° F.

Gradual pressure and temperature increases are made maintaining with each step increase the maximum temperature gradient across a catalyst bed consistent with the necessity of maintaining the thermal stability of the reactor. The reaction rate, and consequent heat release from the catalyst bed is very sensitive to pressure and temperature increases and consequently care must be taken in making these adjustments to avoid temperature destabilization. The gradual upward pressure and temperature adjustments are continued, consistent with maintaining the thermal stability of the reactor until, at the end of these incremental pressure and temperature increases, line-out temperature is achieved, as well as the desired space-time-yield by the reactor.

During start-up the bed, or beds, of catalyst are heated up in localized areas producing hot spots, and consequently temperature profiles occur across a catalyst bed. Transient instabilities exist due to these temperature profiles and, if more heat is produced than can be removed by the heat removal mechanism of bed conduction and interphase heat transfer, an uncontrollable reaction or temperature runaway can occur. Thus, the inherent instabilities of the temperature profile during start-up are due to the transient response to the reaction rate (heat generation).

Alternatively, the temperature can be first increased to line-out temperature, and the pressure then increased to line-out pressure, or the reverse sequence can be employed, or both pressure and temperature alternatively can be gradually adjusted to line-out pressure and line-out temperature, respectively, while the molar ratio of hydrogen:carbon monoxide is maintained at low value. The reaction is much more rapidly quenched, responsive, and readily controlled by changes in the molar ratio of hydrogen:carbon monoxide, at elevated temperature and pressure, than to changes in pressure and/or temperature, at high ratios of hydrogen:carbon monoxide. Hence, in accordance with this invention pressure and temperature are first adjusted each to or approximating its value, respectively, at line-out, and thereafter the ratio of the hydrogen:carbon monoxide is gradually or incrementally increased from a low molar ratio of hydrogen:carbon monoxide to its line-out value. By conducting start-up in this manner the conventional time period required for start-up can be drastically reduced, e.g., from an 8 to 18 day start-up period for a small reactor to as little as about 20 hours, or less.

In initiating the first step (i), the catalyst is contacted with the feed, suitably a mixture of hydrogen and carbon monoxide. The total flow rate relative to temperature, pressure, and the feed ratio of the hydrocarbon and carbon monoxide one relative to the other, is the most insensitive in controlling and stabilizing heat release from the reactor. Consequently, in initiating start-up the flow rate of the gas is set at a very high value. The flow rate of the total feed gas to the reactor is set, on initiation of start-up, to approximate from about 30 percent to about 100 percent, preferably from about 70 to about 100 percent, of that at which the feed is introduced after line-out of the reactor, based on total volume of feed. In setting the flow rate of the feed, hydrogen is maintained at concentration ranging from about 15 percent to about 90 percent, preferably from about 50 percent to about 80 percent, of the concentration of hydrogen present in the feed at line-out, while substantially the balance of the gas component of the feed is carbon monoxide. Preferably, on initiation of start-up the concentration of the carbon monoxide component of the feed is maintained at near or substantially its line-out concentration.

With the feed gas flowing into the reactor, initially at temperature ranging from about 0 to about 200 Fahrenheit degrees, preferably about 10 to about 30 Fahrenheit degrees, below its line-out temperature, the pressure, initially set at values ranging from about 60 to about 550 psig, preferably about 60 psig to about 200 psig below line-out pressure, is incrementally or gradually raised until line-out pressure or pressure approximating line-out pressure is achieved. The temperature is then gradually or incrementally raised to line-out temperature, or temperature approximating line-out temperature. Preferably, the pressure is raised to line-out pressure, and then temperature is raised to line-out pressure in that order; though the reverse order can be followed, or both temperature and pressure can be alternately incrementally or gradually increased to the line-out value of each, respectively.

The molar ratio of the hydrogen:carbon monoxide on initially setting the gas flow rate of the feed in step (i) is maintained at a value below that employed after line-out of the reactor. The hydrogen and carbon monoxide gases, depending upon the nature of the catalyst and the selected reaction conditions, are generally fed after line-out of the reactor in molar ratio of hydrogen:carbon monoxide ranging above about 1.0:1 to about 3:1, ideally, for an ideal catalyst, about 2.08:1. Since ideal catalysts coupled with the use of ideal conditions rarely exist, however, the molar ratio of hydrogen:carbon monoxide after line-out of the reactor is generally found to range above 1.0:1 to about 3:1. In conducting the start-up operation therefore, an initially low molar ratio of hydrogen:carbon monoxide is employed, and during start-up the molar ratio of hydrogen:carbon monoxide is increased from a value ranging from about 90 percent, or less, preferably from about 75 percent, or less, of the molar ratio of hydrogen:carbon monoxide at line-out. Typically the molar ratio of hydrogen:carbon monoxide is raised up to about 1.0:1 to about 3:1, preferably from about 1.7:1 to about 2.1:1.

Thus, with the gas flow rate near that of line-out, and both the temperature and pressure adjusted to line-out conditions, the molar ratio of hydrogen:carbon monoxide is gradually increased, preferably incrementally, consistent with maintaining thermal stability, until the desired hydrogen:carbon monoxide consumption ratio and space-time-yield have been obtained.

In accordance with this procedure the conditions of line-out can be achieved far more quickly than with known prior start-up techniques. In the final step of the start-up process, wherein the molar ratio of the hydrogen:carbon monoxide is increased up to the feed ratio employed at line-out, the catalyst bed temperatures are not significantly perturbed and steady state profiles can be achieved very rapidly. Indeed the over all start-up period for a small reactor can be reduced, in many operations, to 20 hours, or less, which is sharp contrast to the 8 to 18 days required for conventional start-up operations employing a similar reactor.

Another benefit associated with this start-up technique is the flexible response which is offered in a potential or developing runaway situation. Should such adverse development begin to occur, the hydrogen:carbon monoxide feed gas ratio can be decreased in a relatively short time by lowering the hydrogen input (or increasing the carbon monoxide input) to the reactor to effectively quench the reaction rate thereby suppressing the reaction and avoiding the runaway. Minor adjustments can then be made in the temperature or pressure, or both, and the start-up then resumed with a minimum of lost time. In contrast, with the fixed ratio start-up technique the reactor pressure or temperature, or both, must be lowered to suppress and avoid a runaway. The reactor system, however, responds to temperature reductions and pressure reductions quite slowly, considerably slower than is the response to reductions in the molar ratio of hydrogen:carbon monoxide. Moreover, changes in either of these process variables is time consuming and requires beginning over the start-up procedure.

Various well known Fischer-Tropsch synthesis catalysts are useful in the practice of this invention exemplary of which are those constituted of the Group VIII non-noble metals, iron, cobalt, and nickel and Group VIII noble metals, exemplary of which is ruthenium. The catalytic metals can be supported or unsupported, but preferably the metals are supported upon a refractory inorganic oxide base, or admixture of refractory inorganic osides, exemplary of which is kieselguhr, alumina, titania or the like. A ruthenium-titania or cobalt-titania catalyst is preferred. A cobalt-titania catalyst is particularly useful, especially one promoted with thoria, rhenium, hafnium, cerium, niobium, or uranium; more particularly when the titania, or titania portion of the titania-containing support is one having a rutile:anatase weight ratio of at least about 2:3, as determined by ASTM D 3720-78: Standard Test Method for *Ratio of Anatase to Rutile In Titanium Dioxide Pigments By Use of X-Ray Diffraction.* A preferred, and more selective catalyst is one which contains a rutile:anatase ratio of at least about 3:2; generally from about 3:2 to about 100:1, or greater, and more preferably from about 4:1 to about 100:1, or greater. The cobalt, or cobalt and the metal, or metals, added as a promoter is dispersed on the support in catalytically effective amounts.

In terms of absolute concentration, suitably, the metal, or metals, e.g., cobalt, is dispersed on the support in amounts ranging from about 2 percent to about 25 percent, preferably from about 5 percent to about 15 percent, based on the total weight of the catalyst composition (dry basis). The promoter metal is dispersed on the support in amounts ranging from about 0.1 percent to about 10 percent, preferably from about 0.5 percent to about 5 percent, based on the total weight of the catalyst composition (dry basis). Suitably, the metal promoted cobalt catalyst contains Co and promoter metal in ratio of Co:promoter metal ranging from about 20:1 to about 1:1, preferably from about 15:1 to about 2:1, based on the weight of the total amount of Co and promoter metal contained on the catalyst. These catalyst compositions, it has been found, produce at reaction conditions a product which is predominately $C_{10}+$ linear paraffins and olefins, with very little oxygenates. These catalysts provide high selectivity, high activity and good activity maintenance in the conversion of carbon monoxide and hydrogen to distillate fuels.

These catalysts can, e.g., be prepared by gellation, or cogellation techniques. Suitably, e.g., cobalt can be composited alone, or with the promoter metal, upon a previously pilled, pelleted, beaded, extruded, or sieved titania or titania-containing support by the impregnation method. In preparing catalysts, the metal, or metals, is deposited from solution on the support to provide the desired absolute amount of the metal, or metals. Suitably, e.g., cobalt is composited with the support by contacting the support with a solution of a cobalt-containing compound, or salt, e.g., a nitrate, carbonate or the like. The promoter metal, where a promoter metal is to be added, can then be composited with the support in similar manner, or the promoter metal can first be impregnated upon the support, followed by impregnation of the cobalt. Optionally, the promoter metal and cobalt can be co-impregnated upon the support. The cobalt compounds used in the impregnation can be any organometallic or inorganic compound which decomposes to give cobalt oxide upon calcination, such as cobalt nitrate, acetate, acetylacetonate, naphthenate, carbonyl, or the like. Cobalt nitrate is especially preferred while cobalt halide and sulfate salts should generally be avoided. The salts may be dissolved in a suitable solvent, e.g., water, or hydrocarbon solvent such as acetone, pentane or the like. The amount of impregnation solution used should be sufficient to completely immerse the carrier, usually within the range from about 1 to 20 times the carrier by volume, depending on the concentration of the cobalt-containing compound in the impregnation solution. The impregnation treatment can be carried out under a wide range of conditions including ambient or elevated temperatures.

The catalyst, after impregnation, is dried by heating at a temperature above about 32° F., preferably between 32° F. and 255° F., in the presence of nitrogen or oxygen, or both, in an air stream or under vacuum. It is necessary to activate the cobalt-titania, or promoted cobalt-titania catalyst prior to use. Preferably, the catalyst is contacted with oxygen, air, or other oxygen-containing gas at temperature sufficient to oxidize the cobalt and convert the cobalt to $Co_3O_4$. Temperatures ranging above about 300° F., and preferably above about 390° F. are satisfactory to convert the cobalt to the oxide. Suitably, the oxidation of the cobalt is achieved at temperatures ranging from about 300° F. to about 570° F. The metal, or metals, contained on the catalyst are then reduced. Reduction is performed by contact of the catalyst, whether or not previously oxidized, with a reducing gas, suitably with hydrogen or a hydrogen-containing gas stream at temperatures above about 390° F.; preferably above about 480° F. Suitably, the catalyst is reduced at temperatures ranging from about 390° F. to about 930° F. for periods ranging from about 0.5 to about 24 hours at pressures ranging from ambient to about 40 atmospheres. A gas containing hydrogen and inert components in admixture is satisfactory for use in carrying out the reduction.

The conditions employed for operation of a typical reactor after line-out, employing catalysts such as described, are given in terms of the major operating variables as follows:

| Major Operating Variables | Typical Process Conditions | Preferred Process Conditions |
| --- | --- | --- |
| Pressure, Psig | 80–600 | 140–400 |
| Reactor temperature, °F. | 320–560 | 350–500 |
| Gas Feed Rate, GHSV | 100–5000 | 300–2000 |
| Molar Ratio H$_2$:CO | 1.0:1–3:1 | 1.7:1–2.1:1 |

DEMONSTRATION AND EXAMPLES

In conducting the runs for the following demonstration and certain of the examples a ½ inch ID, 6 foot in length tubular steel reactor (constituted of two 3 foot sections connected in series) was employed. The two serially connected sections were immersed in a bath of fluidized sand. Both the sand bath and internal portions of the reactor were provided with thermocouples for monitoring temperature, and air was fed into the bottom of the sand both to maintain the sand in a fluidized state. Electrical wire heaters were provided for input of heat into the sand bath, and analyses of the products from the reactor were made by G.C. The reactor employed in an individual run was charged with a 150 gram portion of a rhenium promoted cobalt-titania catalyst (12% Co; 0.5% Re) prepared by the following procedure:

Titania (Degussa P-25 TiO$_2$) was used as the support after mixing with a stearin lubricant after pilling, grinding, and screening to 80–150 mesh (Tyler). The titania was calcined in air and reduced with hydrogen at 930° F. providing a support containing a rutile:anatase ratio of 50:1 (ASTM D3720-78) a surface area of 12 m$^2$/g and a pore volume of 0.10 ml/g. Catalysts of 80–150 mesh size were prepared by simple impregnation of the support with cobalt and rhenium metals from an acetone/water solution using a rotary evaporator, and drying in a vacuum at 300° F. The catalysts were charged to the reactor, reduced in hydrogen for four hours and then reacted with a synthesis gas. The space-time-yield in conducting the runs was measured as moles of carbon monoxide consumed per liter of catalyst per hour. The temperature across the fixed catalyst bed was measured by a thermocouple located at the inlet side of the reactor and another located at the outlet side of the reactor, the normalized position along the length of the catalyst bed being "0" at the inlet side and "1.0" at the outlet side of the bed; intermediate distances across the catalyst bed being measured proportionately between the values 0 and 1.0 by intermediately located thermocouples. The temperature produced by reaction within the catalyst bed is measured as the difference between the reactor temperature and the temperature of the sand bath, or coolant. In the data given in the demonstration and examples which follow all parts are in terms of weight units except as otherwise specified. Feed compositions are expressed in terms of molar ratios of the components.

Demonstration (Conventional Start-Up)

Conventional wisdom would keep the molar ratio of the hydrogen:carbon monoxide of the feed at a high value, and constant during start-up. The space-time yield of the reactor is then increased by increasing both pressure and temperature. This demonstration illustrates the stability problems encountered with the conventional start-up.

Figure 1:
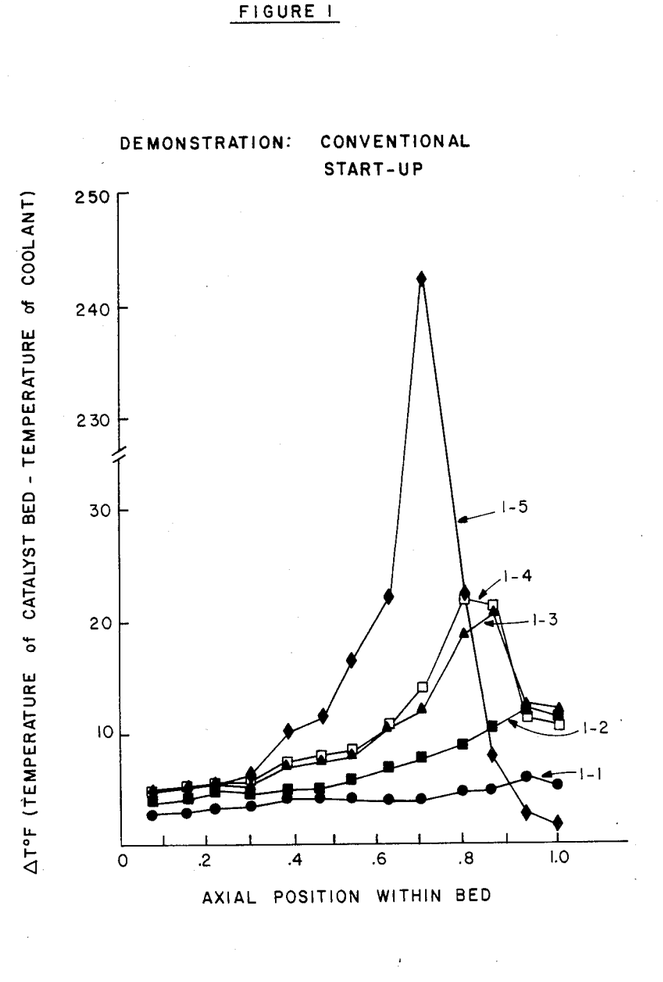

A run was initiated, and a series of five separate conditions were imposed during this run. The conditions of operation and data obtained from each change of condition is given in Table I, summarized in Table IA below, and graghically illustrated by reference to FIG. 1. In FIG. 1 five curves are depicted, each being representative of a change in reaction conditions. In interpreting the graph, the horizontal axis (X-axis) is scaled in proportion to the location within the catalyst bed of the thermocouple from which the temperature was read, zero representing the entry side of the catalyst bed, or side wherein the feed was introduced, with 1.0 representing the gas exit side of the catalyst bed. The differential temperature, ΔT, recorded on the vertical axis (Y-axis) is a plot representative of the difference between the temperature taken within the catalyst bed at a given location therein (as plotted on the horizontal scale) and the temperature of the coolant, or sand bath.

The start-up conditions, and the changes made in the operation of the reactor unit to demonstrate the effect of these changes as given in Table I, and graphically illustrated in FIG. 1, are specifically described below.

TABLE I

| | DEMONSTRATION 1 | | | | | | | | | |
| --- | --- | --- | --- | --- | --- | --- | --- | --- | --- | --- |
| | Condition 1 (Curve 1-1) | | Condition 2 (Curve 1-2) | | Condition 3 (Curve 1-3) | | Condition 4 (Curve 1-4) | | Condition 5 (Curve 1-5) | |
| Axial Position X-Axis | Temp. Catalyst Bed, °F. | ΔT °F. Temp. Cat Bed-Temp. Coolant | Temp. Catalyst Bed, °F. | ΔT °F. Temp. Cat Bed-Temp. Coolant | Temp. Catalyst Bed, °F. | ΔT °F. Temp. Cat Bed-Temp. Coolant | Temp. Catalyst Bed, °F. | ΔT °F. Temp. Cat Bed-Temp. Coolant | Temp. Catalyst Bed, °F. | ΔT °F. Temp. Cat Bed-Temp. Coolant |
| 0.077 | 339.5 | 2.5 | 341 | 4 | 357 | 4 | 359 | 4 | 363 | 4 |
| 0.153 | 339.6 | 2.6 | 341 | 4 | 358 | 5 | 360 | 5 | 364 | 5 |
| 0.23 | 340 | 3.0 | 341.5 | 4.5 | 358.5 | 5.5 | 361 | 6 | 365 | 6 |
| 0.307 | 340 | 3.0 | 341 | 4 | 359 | 6 | 361 | 6 | 366 | 6 |
| 3.384 | 341 | 4 | 341.5 | 4.5 | 360 | 7 | 362 | 7 | 369 | 10 |
| 0.46 | 341 | 4 | 341.8 | 4.8 | 360.5 | 7.5 | 363 | 8 | 370 | 11 |
| 0.538 | 341 | 4 | 342.5 | 5.5 | 361 | 8 | 364 | 9 | 375 | 16 |
| 0.615 | 341 | 4 | 343 | 6 | 363 | 10 | 366 | 11 | 381 | 22 |
| 0.692 | 341 | 4 | 344 | 7 | 365 | 12 | 369 | 14 | 602 | 243 |
| 0.77 | 341.5 | 4.5 | 345 | 8 | 372 | 19 | 377 | 22 | 381 | 22 |
| 0.846 | 341.8 | 4.8 | 347 | 10 | 373 | 20 | 376 | 21 | 367 | 8 |
| 0.923 | 343 | 6 | 349 | 12 | 365 | 12 | 366 | 11 | 362 | 3 |
| 1.00 | 342 | 5.0 | 348 | 11 | 364 | 11 | 365 | 10 | 361 | 2 |
| Temperature Coolant: | 337° F. | | 337° F. | | 353° F. | | 355° F. | | 359° F. | |

(1) In conducting the first run the feed was introduced into the reactor at the target (lined out) feed rate and ratio. The temperature of the coolant medium is at or below that of the lined out value. The pressure of the reactor is at or below that of the lined out value.

The molar ratio of hydrogen:carbon monoxide of the feed gas was maintained at 2.08:1, and the feed was introduced at a rate corresponding to 1000 GHSV. The reactor pressure was maintained at about 60 psig and the coolant temperature was kept at the low value of 337° F. Reference is made to FIG. 1, specifically to the curve depicted by the solid circles (i.e., Curve 1-1). The space-time-yield at these mild conditions, it will be observed, is very low (~2.7) and the temperature rise is very small.

(2) Practical experience shows that one should increase pressure first before temperature during start-up. This is because it is generally more difficult to increase pressure in a slow and controlled rate as compared to temperature.

In this second condition, depicted graphically in FIG. 1 as the curve generated by the solid squares (Curve 1-2), the pressure was slowly increased from 60 psig to 280 psig over a 6 hour period while maintaining the coolant temperature at 337° F. The space-time-yield of the reactor increased to 3.6 and the magnitude of the temperature gradient increased along the entire length of the reactor. The reactor was held at these conditions for 3 days in order to ensure the system was at steady state.

Once the desired lined out reactor pressure is obtained, conventional wisdom would require that one needs only to increase the coolant temperature in order to obtain the lined out (or maximum) space-time-yield.

(3) In this third change in reaction conditions, the coolant temperature was increased from 337° F. to 353° F. over a 24 hour period. During this time the pressure, feed rate, and feed ratio were held constant.

The space-time-yield increased from 3.6 to 9.2 due to the temperature increase. The reactor temperature rise is now more pronounced as shown in FIG. 1 by the curve depicted by the solid triangles (Curve 1-3).

(4) The temperature is further increased in a fourth change in reaction conditions in order to increase the space-time-yield. The curve depicted in FIG. 1 by the open squares (Curve 1-4) shows the temperature profile obtained with a coolant temperature of 355° F. At this point it is necessary to heat the reactor very slowly (about 3° F./hr) in order to avoid any transient instabilities in the reactor temperature which can lead to thermal runaways.

(5) The reactor temperature in a fifth change in reaction conditions was further increased in order to achieve a higher space-time-yield. The temperature, of the catalyst bed was increased from 355° to 359° F. over a 2 hour period. This condition is depicted by the curve shown by the solid diamonds (Curve 1-5). Even with this slow rate of heat up, the reactor experienced a temperature runaway due to the temperature instabilities brought about by this method of start-up. This temperature excursion resulted in a serious loss of catalyst activity and reactor productivity.

TABLE IA

|  | Condition No. | | | | |
| --- | --- | --- | --- | --- | --- |
|  | 1 | 2 | 3 | 4 | 5 |
| Curve No. | 1-1 | 1-2 | 1-3 | 1-4 | 1-5 |
| Temperature coolant, °F. | 337 | 337 | 353 | 355 | 359 |
| Pressure, psig | 60 | 280 | 280 | 280 | 280 |
| Max Temperature Rise, °F. | 8 | 12 | 21 | 22 | 242(1) |
| Space-time-yield | 2.7 | 3.6 | 9.2 | 9.4 | 14(2) |

$$\frac{\text{Moles CO Converted}}{\text{Liter Cat-hr}}$$

(1)Unstable temperature profile.
(2)All the CO in the feed is converted because of the temperature runaway. However, the product slate is principally $CH_4$ and $CO_2$.

EXAMPLE I

During start-up the heat generation rate (rate of CO consumption) is changing with time as the space-time-yield is increased. This example, the data of which are given in Table II, summarized in Table IIA, and graphically illustrated by reference to FIG. 2, demonstrates a start-up technique which drastically reduces the risk of a thermal runaway during the dynamic period of reactor start-up.

TABLE II

EXAMPLE 1

| Axial Position X-Axis | Condition 1 (Curve 2-1) | | Condition 2 (Curve 2-2) | | Condition 3 (Curve 2-3) | | Condition 4 (Curve 2-4) | | Condition 5 (Curve 2-5) | |
| --- | --- | --- | --- | --- | --- | --- | --- | --- | --- | --- |
|  | Temp. Catalyst Bed, °F. | ΔT °F. Temp. Cat Bed- Temp. Coolant | Temp. Catalyst Bed, °F. | ΔT °F. Temp. Cat Bed- Temp. Coolant | Temp. Catalyst Bed, °F. | ΔT °F. Temp. Cat Bed- Temp. Coolant | Temp. Catalyst Bed, °F. | ΔT °F. Temp. Cat Bed- Temp. Coolant | Temp. Catalyst Bed, °F. | ΔT °F. Temp. Cat Bed- Temp. Coolant |
| 0.077 | 355 | 1 | 355 | 1 | 375.5 | 1.5 | 377 | 3 | 378 | 4 |
| 0.153 | 355 | 1 | 355.2 | 1.2 | 376 | 2 | 377.5 | 3.5 | 378.5 | 4.5 |
| 0.23 | 355 | 1 | 355.5 | 1.5 | 378 | 4 | 378 | 4 | 379 | 5 |
| 0.307 | 355.8 | 1.8 | 356 | 2 | 378.5 | 4.5 | 379 | 5 | 380 | 6 |
| 3.384 | 356.2 | 2.2 | 356.4 | 2.4 | 382 | 8 | 382 | 8 | 383 | 9 |
| 0.46 | 356.5 | 2.6 | 356.6 | 2.6 | 383 | 9 | 383 | 9 | 385 | 11 |
| 0.538 | 356.8 | 2.8 | 357 | 3 | 388 | 14 | 390 | 16 | 392 | 18 |
| 0.615 | 357 | 3 | 357.5 | 3.5 | 389 | 15 | 393 | 19 | 397 | 23 |
| 0.692 | 357.2 | 3.2 | 358 | 4 | 390 | 16 | 396 | 22 | 398 | 24 |
| 0.77 | 357.5 | 3.5 | 358.5 | 4.5 | 382 | 8 | 383 | 9 | 381 | 7 |
| 0.846 | 358 | 4 | 360 | 6 | 378 | 4 | 380 | 6 | 378 | 4 |
| 0.923 | 358.5 | 4.5 | 359 | 5 | 376 | 2 | 377 | 3 | 376 | 2 |
| 1.00 | 359 | 5 | 362 | 8 | 377 | 3 | 378 | 4 | 377 | 3 |
| Temperature Coolant: | 354° F. | | 354° F. | | 374° F. | | 374° F. | | 374° F. | |

Figure 2:
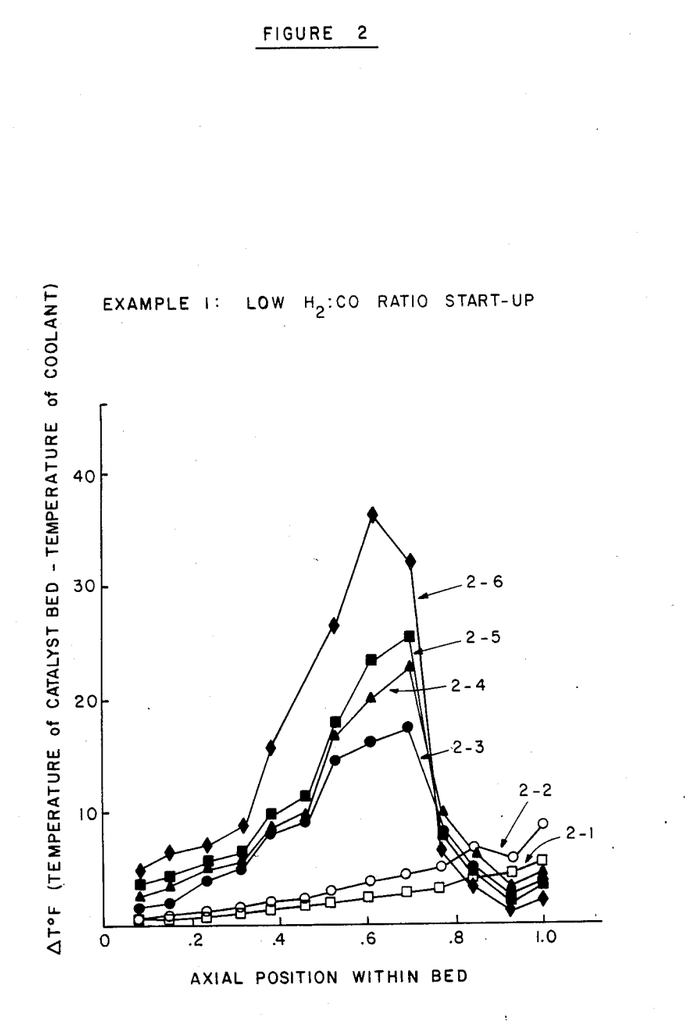

(1) The feed is introduced into the reactor at a low temperature and pressure and the molar ratio of the hydrogen:carbon monoxide in the feed is well below that desired at preferred line-out conditions (1.7:1 vs. 2.1:1). Reference is made to FIG. 2, specifically to Curve 2-1 depicted by open squares which graphically illustrates this run. The feed gas rate is slightly lower than that of the line-out conditions (910 vs 1000 GHSV)

though this has no significant effect on the reactor transients during start-up.

At these mild conditions (temperature coolant=354° F., pressure=60 psig) the space-time-yield of the reactor is quite low (2.0).

(2) Using a feed wherein the molar ratio of hydrogen:carbon monoxide is 1.7:1, and constant coolant temperature, the reactor pressure was increased to 280 psig over a fairly short time period (~0.5 hrs). Both the space-time-yield and catalyst bed temperature increased. Reference is made to FIG. 2, specifically to the curve (2-2) depicted by the open circles.

(3) At a constant molar feed ratio hydrogen:carbon monoxide and reactor pressure, the coolant temperature was increased from 354° F. to 374° F. over a one hour period. The space-time-yield increased from 3.0 to 8.8 and the catalyst bed temperature increased markedly. Reference is made to FIG. 2, and to Curve 2-3 depicted by the solid circles.

(4) At a constant reactor pressure and coolant temperature the hydrogen:carbon monoxide molar feed ratio was increased from 1.7:1 to 2.0:1. The ratio change was made very quickly (~1 min) by increasing the $H_2$ flow relative to the CO flow, the total gas flow rate increasing from 910 GHSV to 970 GHSV. This change resulted in an increase in both the space-time-yield (from 8.8 to 9.6) and catalyst bed temperature. Reference is made to FIG. 2, Curve 2-4, these data being graphically depicted by the solid triangles illustrative of the temperature profile.

(5) The molar feed ratio of hydrogen:carbon monoxide was further increased from a value of 2.0:1 to 2.1:1. This change was made in the identical fashion as in setting the 4th condition to produce Curve 2-4. The gas flow rate increased from 970 GHSV to 1000 GHSV. The space-time-yield increased from 9.6 to 10.5. The temperature profile obtained at the 2.1$H_2$/CO feed ratio is best illustrated by reference to FIG. 2, specifically to the curve defined by the solid squares (Curve 2-5).

The space-time-yield obtained using the low molar ratio $H_2$:CO start-up procedure is clearly much higher than that obtained using the conventional fixed ratio procedure (10.5 in this case versus 9.4 in the Demonstration (Curve 1-4).

(6) Using the low molar hydrogen:carbon monoxide start-up procedure it is possible to obtain space-time-yields which are much higher than those obtainable with the conventional fixed ratio procedure. Reference is made to FIG. 2, specifically to 2-6 (solid diamonds) which illustrates the temperature profile obtained at a space-time-yield of 13.0. This high reactor productivity was obtained by following the procedure and conditions defined by Curves 2-2, 2-4, and 2-5, except that the coolant temperature was held at a higher value of 380° F. The higher productivities obtained using the low ratio procedure are a direct result of maintaining stable temperature profiles during start-up. Using the fixed ratio start-up procedure, space-time-yields which exceed $$9.4 \frac{\text{moles CO converted}}{\text{liter cat-hr}}$$

can lead to temperature instabilities which cause temperature runaways.

TABLE IIA

| | Condition No. | | | | | |
|---|---|---|---|---|---|---|
| | 1 | 2 | 3 | 4 | 5 | 6 |
| Curve No. | 2-1 | 2-2 | 2-3 | 2-4 | 2-5 | 2-6 |
| $H_2$/CO Feed Ratio | 1.8:1 | 1.8:1 | 1.8:1 | 2.0:1 | 2.1:1 | 2.1:1 |
| $T_{coolant}$, °F. | 354 | 354 | 374 | 374 | 374 | 380 |
| Pressure, psig | 60 | 280 | 280 | 280 | 280 | 280 |
| Max Temperature Rise, °F. | 7 | 9 | 17 | 23 | 25 | 35 |
| Space-time-yield | 2.0 | 3.0 | 8.3 | 9.6 | 10.5 | 13.0 |

$$\frac{\text{Moles CO Converted}}{\text{Liter Cat-hr}}$$

Process upsets in pressure, temperature, and feed rate can readily perturb the steady state temperature profile and create a thermal runaway. For example, a small plug in the exit line or a small perturbation in the back pressure control system of the reactor can lead to a small pressure perturbation which in turn can cause a temperature instability in the catalyst bed. Small transient perturbations in the coolant temperature brought about, e.g., by momentary failures in the instrument control loop can also cause temperature instabilities.

In general, any process upset which causes a transient perturbation in the CO reaction rate, can also cause a temperature instability in the catalyst bed. Many of these types of process upsets are quite transient in nature. In commercial practice the variable (i.e., coolant temperature or pressure) may undergo a change from the desired steady state or lined-out value for a short period of time and then quickly return to its original value. (For example when switching process streams in an integrated process.)

Any process upset which results in an unstable catalyst bed temperature profile may thus ultimately lead to a temperature runaway. In conventional practice, one would have to "shut down" the unit in order to avoid this occurrence. This involves dropping either or both reactor pressure or coolant temperature. Such action would avoid the potential runaway situation before it develops. In typical pilot plant reactor systems, wherein the reactor diameters are very large, waiting to see if the runaway situation will develop or not during a process upset can be extremely hazardous. This is because the dynamics of the reactions involved in the thermal runaway are faster than the time it takes to drop either or both the reactor pressure and coolant temperature. For a typical small pilot plant (reactor diameter=½"; length=7') it will require at least a couple of minutes in order to decrease the reactor pressure a couple of hundred pounds. Temperature changes are typically an order of magnitude slower. The time required to reach the high temperature of an exothermic runaway in a small reactor is typically much less than one minute.

A large pilot plant or commercial size unit (diameter ≧1" and/or; length≧10') requires an even longer period of time to drop the temperature and/or pressure and the attainment of high temperature in the catalyst bed. The time required to reach these high temperatures is nonetheless typically less than one minute since the kinetics of the runaway chamical reactions is independent of the reactor size. However, these larger units contain huge volumes of gas and large heat capacities due to the construction metal. Consequently one cannot quickly nor readily drop the pressure and/or temperature quickly enough to avoid an exothermic runaway.

EXAMPLE 2

This example illustrates the speed at which a thermal runaway can occur in a pilot plant unit having a ½" diameter, 2.2 foot in length reactor. Table III provides data obtained during a run at four different conditions, depicted in FIG. 3 as Curves 3-1, 3-2, 3-3, and 3-4, respectively. Condition 1 (depicted by Curve 3-1) was made at time "0" with the pressure at 280 psig and coolant temperature of 410° F.; Condition 2 (depicted by Curve 3-2) was made at time "3 minutes" into the run with pressure at 320 psig and coolant temperature of 410° F.; Condition 3 (depicted by Curve 3-3) was made at time "4 minutes" into the run with pressure at 320 psig and coolant temperature at 410° F.; and in Condition 4 (depicted by Curve 3-4) wherein control of the reaction is effected, the time is 5.5 minutes into the run from time zero.

TABLE III

| Axial Position X-Axis | Condition 1 (Curve 3-1) | | Condition 2 (Curve 3-2) | | Condition 3 (Curve 3-3) | | Condition 4 (Curve 3-4) | |
|---|---|---|---|---|---|---|---|---|
| | Temp. Catalyst Bed, °F. | ΔT °F. Temp. Cat Bed-Temp. Coolant | Temp. Catalyst Bed, °F. | ΔT °F. Temp. Cat Bed-Temp. Coolant | Temp. Catalyst Bed, °F. | ΔT °F. Temp. Cat Bed-Temp. Coolant | Temp. Catalyst Bed, °F. | ΔT °F. Temp. Cat Bed-Temp. Coolant |
| 0.083 | 413 | 3 | 413 | 3 | 413 | 3 | 409 | 1 |
| 0.167 | 413.5 | 3.5 | 413.5 | 3.5 | 414 | 4 | 409 | 1 |
| 0.25 | 414 | 4 | 414 | 4 | 415 | 5 | 410 | 2 |
| 0.33 | 417 | 7 | 420 | 10 | 418 | 8 | 410 | 2 |
| 0.417 | 424 | 14 | 427 | 17 | 427 | 17 | 410 | 2 |
| 0.50 | 427 | 17 | 427 | 17 | 426 | 16 | 412 | 4 |
| 0.583 | 431 | 21 | 426 | 26 | 710 | 300 | 613 | 205 |
| 0.667 | 427 | 17 | 428 | 18 | 417 | 7 | 410 | 2 |
| 0.75 | 423 | 13 | 423 | 13 | 411 | 1 | 409.5 | 1.5 |
| 0.833 | 416 | 6 | 416 | 6 | | — | 409 | 1 |
| 0.917 | 413 | 3 | 413 | 3 | 410.5 | 0.5 | 408.5 | 0.5 |
| 1.00 | 414 | 4 | 414 | 4 | | 0 | 408 | 0 |
| Temperature Coolant = | 410° F. | | 410° F. | | 410° F. | | 408° F. | |

Figure 3:
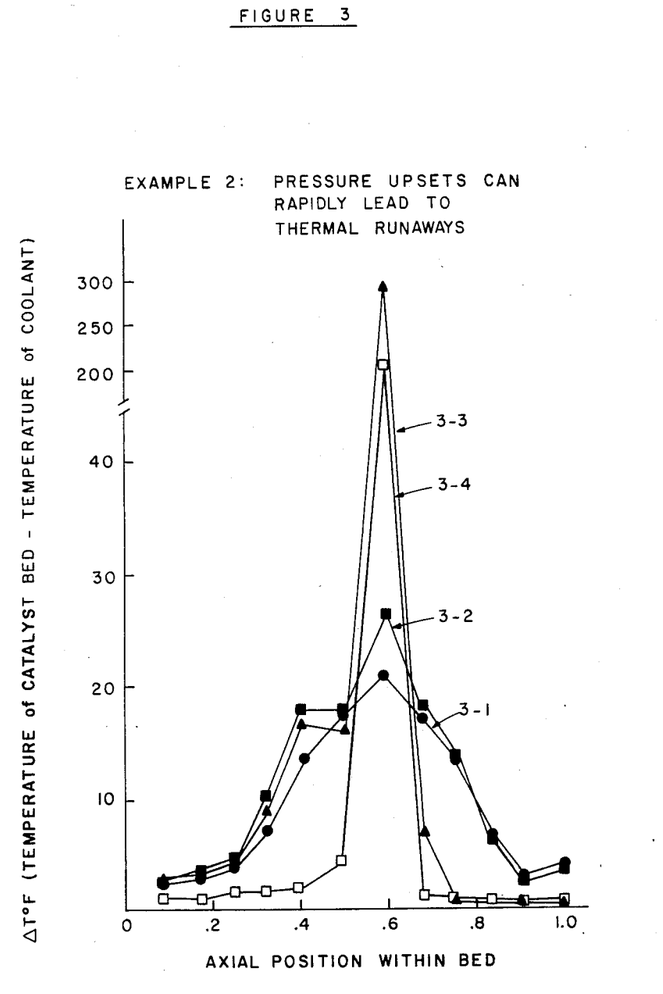

(1) In this run, Run 3, the catalyst was operating at lined-out conditions which had a catalyst bed temperature profile shown by reference to FIG. 3, Curve 3-1 depicted by the solid circles. During this period, the reactor was operated at a pressure of 280 psig, and the temperature of the coolant was 410° F.

(2) During the course of lined-out operations there was a partial flow blockage (plug) at a time "0" in the back end of the unit wherein the product is collected. This is a common type of upset which will occur routinely in synthesis reactor systems which produce heavy hydrocarbons. The partial plug resulted in a step change increase in pressure from 280 to 320 psig. This pressure increase is not in itself a serious upset because the catalyst bed temperatures do not rise immediately in any appreciable amount. This change in condition is illustrated by Curve 3-2 (curve shown by solid squares) which depicts the catalyst bed temperature profile 3 minutes after the upset. At this point the temperature of the catalyst bed is not lined-out at steady state values.

(3) Reference is made to Curve 3-3 (solid triangles) representative of the condition of the catalyst bed after 4 minutes from time "0". The reactor pressure still registers 320 psig, and the temperature of the coolant is 410° F. A hot spot has thus developed four minutes after the pressure upset. In less than 2 minutes time the hot spot temperature went from a moderately low value of 28° F. to a very high value, almost 300° F. This high temperature resulted in the immediate deactivation of the catalyst in this hot zone.

(4) After the high temperature was attained the pressure and temperature of the reactor were lowered immediately. In approximately 1.5 minutes the pressure was decreased from 320 psig to 30 psig and the temperature was decreased from 410° F. to 408° F. However, as graphically depicted in Curve 3-4 (open squares) the hot spot temperature cannot be lowered quickly due to the heat capacity of the catalyst/reactor system and the relatively low heat transfer rates associated with hydrocarbon synthesis catalyst beds. It took approximately 30 minutes for the hot spot to cool down to the coolant temperature at a pressure of 30 psig.

In conventional practice, where a fixed feed ratio is employed, this type of runaway can be avoided by immediately decreasing the temperature and/or pressure as soon as the upset occurs. However, the pressure can seldom be decreased rapidly enough to avoid the exothermic runaway since it can take many minutes to decrease the pressure and/or temperature, especially in large reactors. Thus, once the runaway begins to occur the pressure or temperature cannot be dropped fast enough to avoid the high temperatures and consequently one must drop temperature and/or pressure every time a potential upset is suspected. Operation using a variable $H_2/CO$ feed ratio, however, allows a far more flexible response to process upsets. A unit operated in this manner need not be shut down each time as upset is suspected. Indeed, one can control the temperature profile with far more precision by using the variable $H_2/CO$ feed ratio concept of this invention to control the reaction than by the mere changing temperature and/or pressure as formerly practiced.

Any time a process variable is changed so that the space-time-yield (or heat generation) of the reactor is increased, a temperature runaway is possible. The probability of this event is highest when one is operating the reactor at high space-time-yields as is required to maximize the productivity of the catalyst. The value of the maximum allowable ΔT (temperature difference between the catalyst bed and coolant) depends primarily upon the diameter size of the reactor, radial heat transfer rate, and the nature of the coolant medium. Every reactor system has a maximum operable ΔT at which one can operate in order to get the desired product yield.

Perturbations in important process variables such as temperature and pressure can result in unstable temperature profiles which can lead to exothermic runaways. Conventional wisdom teaches that in order to avoid a temperature runaway must decrease the reactor pressure and/or temperature in order to cool down the hot spot. [Dropping coolant temperature is not feasible in most cases since this action can take many minutes (even in a small pilot plant) to appreciably drop the catalyst bed temperature.] These steps, however, require a long time relative to the time frame of a thermal

EXAMPLE 3

Figure 4:
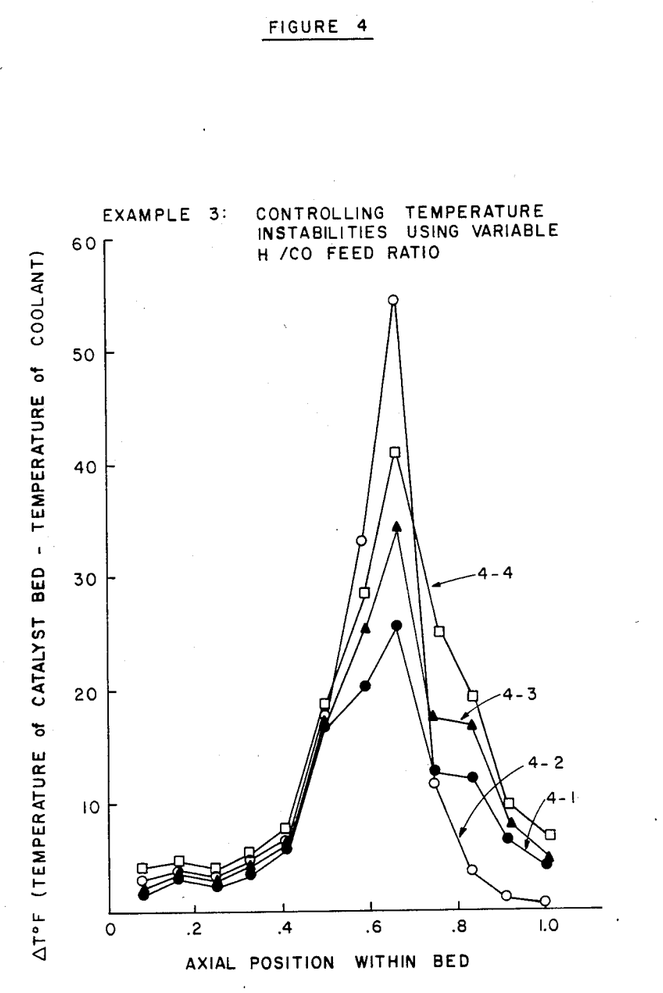

Reference is made to FIG. 4, to Table IV and Table IVA which summarizes the conditions, and data from this run.

TABLE IV

| Axial Position X-Axis | Condition 1 (Curve 4-1) | | Condition 2 (Curve 4-2) | | Condition 3 (Curve 4-3) | | Condition 4 (Curve 4-4) | |
|---|---|---|---|---|---|---|---|---|
| | Temp. Catalyst Bed, °F. | $\Delta T$ °F. Temp. Cat Bed- Temp. Coolant | Temp. Catalyst Bed, °F. | $\Delta T$ °F. Temp. Cat Bed- Temp. Coolant | Temp. Catalyst Bed, °F. | $\Delta T$ °F. Temp. Cat Bed- Temp. Coolant | Temp. Catalyst Bed, °F. | $\Delta T$ °F. Temp. Cat Bed. Temp. Coolant |
| 0.083 | 352 | 2 | 365 | 3 | 365 | 3 | 366 | 4 |
| 0.167 | 353 | 3 | 366 | 4 | 366 | 4 | 367 | 5 |
| 0.25 | 352 | 2 | 365 | 3 | 365 | 3 | 366 | 4 |
| 0.33 | 353 | 3 | 367 | 5 | 366 | 4 | 367 | 5 |
| 0.417 | 356 | 6 | 368 | 6 | 368 | 6 | 369 | 7 |
| 0.50 | 366 | 16 | 379 | 17 | 379 | 17 | 380 | 18 |
| 0.583 | 369 | 19 | 395 | 33 | 387 | 25 | 390 | 28 |
| 0.667 | 375 | 25 | 416 | 54 | 396 | 34 | 403 | 41 |
| 0.75 | 362 | 12 | 373 | 11 | 389 | 27 | 386 | 24 |
| 0.833 | 361 | 11 | 366 | 4 | 388 | 26 | 380 | 18 |
| 0.917 | 356 | 6 | 364 | 2 | 362 | 0 | 371 | 9 |
| 1.00 | 354 | 4 | 363 | 1 | 366 | 4 | 368 | 6 |
| Temperature Coolant = | 350° F. | | 362° F. | | 362° F. | | 362° F. | | runaway. Additionally, such adjustments would result in a total shutdown (loss of productivity) of the synthesis reactor. The reactor thus must be started up again from a low space-time-yield stage, this action consuming valuable process time and causing the upset of all process equipment down-stream of this reactor. A thermal runaway can occur in a very short time frame (less than 2 minutes) and once the high temperatures are achieved in the catalyst bed it will not quickly cool off once the pressure is dropped because of the low heat transfer. In accordance with this invention, however, in situations such as this (where the catalyst bed temperature is not at steady state, nor lined-out and a thermal runaway is possible) one can lower the $H_2/CO$ molar feed ratio thereby improving the stability of the catalyst bed temperature to minimize the possibility of a thermal runaway. Changes in the gas phase composition will effect the rate of heat generation (reaction rate) very quickly. For example, at 1000 GHSV, at a hydrogen:-carbon monoxide molar ratio of 2.08:1, or higher, a ratio change would have a direct impact on the entire catalyst bed in approximately 30 seconds even if the reactor is running at the maximum theoretical space-time-yield (100% CO conversion). In most instances of a thermal runaway the hot spot is not at the reactor exit and the reactor is not running at the maximum theoretical space-time-yield so the response time is much faster than thirty seconds.

Enhanced flexibility in operations is also obtained by adjusting the $H_2/CO$ ratio when obtaining maximum reactor productivity. One can control the temperature profile of the catalyst bed in a more secure and reproducible manner since the temperature profile responds more quickly to ratio changes as opposed to changes in the temperature and pressure.

The following example illustrates how the temperature profile can be controlled by adjusting the $H_2/CO$ feed ratio to provide a more stable and flexible operation. The catalyst bed temperature can thus be readily controlled by adjusting the molar feed ratio so that exothermic runaways can be avoided. This technique also allows a flexible response to a developing upset without having to drastically change process variables such as temperature and pressure.

(1) Specific reference is made to Curve 4-1 (solid circles) which illustrates the catalyst temperature profile at steady state lined-out conditions, i.e., 280 psig, 1000 GHSV.

(2) At this point in time the coolant temperature was raised from 350° F. to 362° F. The increased temperature resulted in a dramatic increase in the magnitude of the hot spot as illustrated by Curve 4-2 depicted by the open circles. The increase in coolant temperature raised the hot spot from 27° F. to 54° F. This perturbation to the temperature profile could lead to a thermal runaway. As previously discussed, a thermal runaway can occur very quickly and once it occurs the adverse change in the catalyst is already consummated, and hence dropping the pressure and/or temperature will only stop the runaway from spreading to other parts of the catalyst bed.

(3) Since a 54° F. hot spot is unacceptably high for this reactor system, the $H_2/CO$ feed ratio was lowered from 1.8:1 to 1.5:1. This decrease in the gas phase kinetic driving force lowered the hot spot temperature from 54° F. (Curve 4-2) to 34° F. as shown in Curve 4-3 depicted by the solid triangles. The time required for the transition from Curve 4-2 to Curve 4-3 was very fast (~1 minute) as would be expected.

(4) At this point the $H_2/CO$ molar bed ratio was increased back to the 1.8:1 value since this was the desired lined-out value. The new lined-out temperature profile is shown by Curve 4-4 depicted by the open squares.

The high hot spot illustrated in Curve 4-2 (54° F.) represented a transient temperature profile brought about by the relative rapid heating of the reactor (12° F./120 minutes). The true lined out hot spot obtained at a 362° F. coolant and a 1.8:1 $H_2/CO$ feed ratio is shown by Curve 4-4. The hot spot obtained in Curve 4-2 due to rapid heating may have cooled down to the lined out value shown in Curve 4-4. However, it may have also led to an exothermic runaway which would have damaged the catalyst.

TABLE IVA

|  | Condition No. | | | |
| --- | --- | --- | --- | --- |
|  | 1 | 2 | 3 | 4 |
| Curve No. | 4-1 | 4-2 | 4-3 | 4-4 |
| H$_2$/CO Feed Ratio | 1.8:1 | 1.8:1 | 1.5:1 | 1.8:1 |
| $\Delta T_{max}$ (hot spot) | 27 | 54 | 34 | 41 |
| Temperature coolant, °F. | 350 | 362 | 362 | 362 |
| Time (Mins.) | 0 | 120 | 121 | 124 |

Process Conditions: 280 psig, 1000 GHSV
Reactor: ½" diameter SCH 80, 2.2' long.

It is apparent that various modifications and changes can be made without departing the spirit and scope of the present invention.

What is claimed is:

1. In a process for the start-up of a reactor wherein a feed comprised of hydrogen and carbon monoxide is contacted with a bed of hydrocarbon synthesis catalyst in which perturbations of the temperature profile across the bed can develop, and which, at line-out conditions defined by feed flow rate, pressure, temperature, and the molar ratio of hydrogen:carbon monoxide of the feed is sufficient to synthesize hydrocarbons from the hydrogen and carbon monoxide, the improvement which comprises: elevating, while maintaining the molar feed ratio of hydroge:carbon monoxide at below about 90 percent of its line-out value, the feed flow rate, pressure, and temperature to values approaching line-out feed flow rate, line-out pressure, and line-out temperature, and then gradually increasing the molar feed ratio of hydrogen:carbon monoxide to essentially that employed at line-out.

2. The process of claim 1 wherein, in initiating start-up the feed is introduced into the reactor at a flow rate ranging from about 30 percent to about 100 percent that at which said feed is introduced into the reactor at line-out.

3. The process of claim 2 wherein the flow rate ranges between about 70 percent to about 100 percent.

4. The process of claim 1 wherin in initiating start-up the hydrogen is introduced into the reactor at from about 15 to about 90 percent of the feed rate of hydrogen employed at line-out.

5. The process of claim 1 wherein, in initiating start-up the molar ratio of hydrogen:carbon monoxide does not exceed about 75 percent of its line-out value.

6. The process of claim 1 wherein after line-out the molar ratio of hydrogen:carbon monoxide ranges from about 1.0:1 to about 3:1.

7. In a process for the start-up of a reactor wherein a feed comprised of hydrogen and carbon monoxide is contacted with a bed of hydrocarbon synthesis catalyst in which perturbations of the temperature profile across the bed can develop, and which, at line-out conditions defined by feed flow rate, pressure, temperature, and the molar ratio of hydrogen:carbon monoxide of the feed is sufficient to synthesize hydrocarbons from the hydrogen and carbon monoxide, the improvement which comprises:

(i) introducing the feed into the reactor at a rate ranging between about 30 percent and 100 percent of the total flow rate at which the feed is introduced to the reactor at line-out, hydrogen being introduced into the reactor as a portion of said feed in molar feed rate ranging from about 15 percent to about 90 percent of the feed rate of hydrogen employed in the reactor at line-out, the molar ratio of hydrogen:carbon monoxide of the feed not exceeding about 90 percent of the molar ratio of hydrogen:carbon monoxide at line-out, (ii) raising the pressure and temperature of the reactor to levels of pressure and temperature, respectively, employed at line-out; and while maintaining these levels of pressure and temperature, (iii) increasing gradually the molar ratio of hydrogen:carbon monoxide until the molar ratio of hydrogen:carbon monoxide is essentially that employed at line-out.

8. The process of claim 7 wherein, in initiating start-up the feed is introduced into the reactor at a flow rate ranging from about 70 percent to about 100 percent that at which said feed is introduced into the reactor at line-out.

9. The process of claim 7 wherein in initiating start-up the hydrogen is introduced into the reactor at from about 50 to about 80 percent of the feed rate of hydrogen employed at line-out.

10. The process of claim 7 wherein, in initiating start-up the molar ratio of hydrogen:carbon monoxide does not exceed about 75 percent of its line-out value.

11. The process of claim 7 wherein after line-out the molar ratio of hydrogen:carbon monoxide ranges from about 1.0:1 to about 3:1.

12. In a process for the start-up of a reactor wherein a feed comprised of hydrogen and carbon monoxide is contacted with a bed of hydrocarbon synthesis catalyst in which perturbations of the temperature profile across the bed can develop, and which, at line-out conditions defined by feed flow rate, pressure, temperature, and the molar ratio of hydrogen:carbon monoxide of the feed is sufficient to synthesize hydrocarbons from the hydrogen and carbon monoxide, the improvement which comprises:

(i) introducing the feed into the reactor at a rate ranging between about 30 percent and 100 percent of the total flow rate at which the feed is introduced to the reactor at line-out, hydrogen being introduced into the reactor as a portion of said feed in molar feed rate ranging from about 15 percent to about 90 percent of the feed rate of hydrogen employed in the reactor at line-out, the molar ratio of hydrogen:carbon monoxide of the feed not exceeding about 90 percent of its line-out value, the temperature ranging from about 0 Fahrenheit degrees to about 200 Fahrenheit degrees below the temperature employed at line-out, pressure ranging from about 60 psig to about 550 psig below the pressure employed at line-out, (ii) increasing gradually the pressure of the reactor to that employed after line-out of the reactor while maintaining substantially the temperature and gas flow rate described in step (i);

increasing gradually the temperature of the reactor until the space-time-yield obtained with the feed gas characterized in step (i) corresponds to that obtained during line-out; and while maintaining these levels of pressure and temperature, (iii) increasing gradually the molar ratio of hydrogen:carbon monoxide until the molar ratio of hydrogen:carbon monoxide is essentially that employed at line-out.

13. The process of claim 12 wherein, in initiating start-up the feed is introduced into the reactor at a flow rate ranging from about 70 percent to about 100 percent that at which said feed is introduced into the reactor at line-out, the hydrogen is introduced into the reactor at from about 50 to about 80 percent of the feed rate of hydrogen employed at line-out, and the molar ratio of hydrogen:carbon monoxide does not exceed about 75 percent of its line-out value.

14. The process of claim 12 wherein after line-out the molar ratio of hydrogen:carbon monoxide ranges between about 1.0:1 to about 3:1.

* * * * *